United States Patent [19]
Gibson et al.

[11] Patent Number: 5,344,914
[45] Date of Patent: Sep. 6, 1994

[54] COMMERCIALLY VALUABLE POLYMERIC KETONES AND METHOD OF PREPARING SAME

[75] Inventors: Harry W. Gibson, Blacksburg, Va.; Ashish Pandya, Natick, Mass.

[73] Assignee: The Center for Innovative Technology*, Herndon, Va.

[21] Appl. No.: 956,743

[22] Filed: Oct. 5, 1992

[51] Int. Cl.$^5$ ............................................. C08G 69/10
[52] U.S. Cl. ............................. 528/328; 528/171; 528/172; 528/173; 528/220; 528/228; 528/310; 528/321
[58] Field of Search ............... 528/328, 310, 321, 220, 528/228, 171, 172, 173

[56] References Cited

U.S. PATENT DOCUMENTS 4,929,713  5/1990  Gibson et al. .................. 528/328

OTHER PUBLICATIONS

R. May in Encyclopedia of Polymer Science and Engineering, J. Wiley and Sons, N.Y., 2nd ed., Jun. 1987, vol. 12, pp. 313–320.
P. A. Staniland in Comprehensive Polymer Science, G. Allen and J. C. Bevington, series eds. Pergamon Press, N.Y., vol. 5, Jun. 1989, pp. 483–497.
Colquhoun, H. et al, J. Chem. Soc., Chem. Commun., 1990, p. 336.
Ueda M. et al, Macromol. Jun. 1990, 23:926.
Johnson et al, Polymer. J. Polym. Sci. A1, Jun. 1967, 5:2375.
Attwood, et al, Polymer, Jun. 1977, 18:354.
Attwood, et al, Polymer, Jun. 1981, 22:1096.
Kircheldorf, et al, Polymer, Jun. 1989, 25:1151.
Kircheldorf, et al. Macromol. Jun. 1989, 22:517.
U.S. Pat. No. 3,442,857; Chem. Abstr. Jun. 1967, 67:44371.
U.S. Pat. 3,516,966; Chem.Abstr. Jun. 1970, 73:35968.
Eur. Patent 63,874; Chem.Abst. Jun. 1983, 98:180081.
Starkweather in Encyclopedia of Polymer Science & Engineering, J. Wiley & Sons, N.Y., 2nd. ed., Jun. 1987, vol. 10, pp. 369–373.
Harris et al, J. Polym. Sci. Poly. Phys. Ed. Jun. 1987, 25:311.
March, Advanced Org. Chem., J. Wiley & Sons, N.Y., 3rd ed., Jun. 1985, pp. 855–856.
Albright, J., Tetrahedron, Jun. 1983, 39:3207.
McEvoy, et al, J. Org. Chem. Jun. 1979, 44:4597.
Albrecht et al., Synthesis, Jun. 1979, p. 127.
Starkweather, H., J. Polym. Sci., Polym. Phys. Ed., Jun. 1977, 15:247.
Stork, et al, Tetrahedron Ltrs., Jun. 1978, 5175.

Primary Examiner—John Kight, III
Assistant Examiner—T. Mosley
Attorney, Agent, or Firm—Whitham, Curtis, Whitham & McGinn

[57] ABSTRACT

A new method for preparing commercially valuable polymeric ketones is described. The method employs an α-amiononitrile as a monomeric unit whereby an amorphous, soluble polymer having protected carbonyl moiety is obtained. Upon deprotecting the carbonyl moiety, a crystalline polymeric ketone is obtained. The method allows production of polymeric ketone materials having aromatic, aliphatic or mixed aromatic/aliphatic backbones.

6 Claims, 8 Drawing Sheets

FIG.3 a: X=C=O, Y=-O-
b: X=C=O, Y=nil
c: X=SO₂, Y=-O-
d: X=SO₂, Y=nil

| R/R |
|---|
| $CH_3/CH_3$ |
| $C_2H_5/CH_3$ |
| $C_2H_5/C_2H_5$ |
| $n\text{-}C_4H_9/n\text{-}C_4H_9$ |
| $-CH_2CH_2OCH_2CH_2-$ |
| $-CH_2CH_2CH_2CH_2CH_2-$ |

FIG. 8

$$R_1 = R_2 = H, \ R_3 = \overset{O}{\underset{\|}{C}}O(CH_2)_x O\overset{O}{\underset{\|}{C}} -$$

$$R_1 = R_2 = H, \ R_3 = \overset{O}{\underset{\|}{C}}NH(CH_2)_x NH\overset{O}{\underset{\|}{C}} -$$

$$R_1 = R_2 = H, \ R_3 = -\overset{O}{\underset{\|}{C}}NH - Ar' - NH\overset{O}{\underset{\|}{C}} -$$

$$R_1 = H, \ R_2 = CH_3, \ R_3 = -\overset{O}{\underset{\|}{C}}O(CH_2)_x O\overset{O}{\underset{\|}{C}} -$$

$$R_1 = H, \ R_2 = CH_3, \ R_3 = -\overset{O}{\underset{\|}{C}}NH(CH_2)_x NH\overset{O}{\underset{\|}{C}} -$$

$$R_1 = H, \ R_2 = CH_3, \ R_3 = -\overset{O}{\underset{\|}{C}}NH - Ar' - NH - \overset{O}{\underset{\|}{C}} -$$

FIG. 9

COMMERCIALLY VALUABLE POLYMERIC KETONES AND METHOD OF PREPARING SAME

The present invention is related generally to the method of synthesizing polymeric ketones. More particularly, the present invention is related to producing novel monomers for the synthesis of new as well as known polymeric ketones. The polymers produced in accordance with the present invention are initially non-crystalline and soluble in ordinary organic media, thereby allowing easy processibility without the use of exotic solvents and high temperatures in order to obtain desirable crystalline end products.

Polymeric ketones are a relatively rare class of materials useful in a number of high performance applications.[1] It should be mentioned, however, that whereas the ketone functionality bestows highly desirable crystalline structure to the polymers, it is also this crystallinity which makes the processing of the polymers a difficult problem, thus limiting the usefulness of these materials.

Heretofore, aromatic polymeric ketones have been made by Friedel-Crafts reactions,[2] ring opening reactions[3] or by nucleophilic substitution,[2] the latter being commonly used in commercial preparations, or coupling of aromatic dihalides.[4] However, it should be noted that nucleophilic substitution does not allow for easy processability[2,5-9] of crystalline polymers and the Friedel-Crafts methodology is quite expensive because of the handling and disposal of large quantities of strong Lewis or Bronstead acids required to maintain solubility of the polyketone.[2,10-12]

Aliphatic polyketones have been made by copolymerization of olefins and CO by both free radical and palladium catalyzed "insertion" polymerizations.[13] A maximum of 50 mole percent CO may be incorporated by these methods.[13]

Thus, it is clear that the currently available synthetic techniques have limited scope and applicability.

SUMMARY OF INVENTION

It is, therefore, an object of the present invention to provide more economical and efficient synthetic methodologies than presently available for the preparation of polymeric ketones.

It is another object of the present invention to provide novel monomers for the synthesis of new and known polymeric ketones.

A further object of the present invention is to provide non-crystalline, easily processable precursor or intermediate polymers which are readily convertible to desired crystalline polyketone materials, for example by acid hydrolysis.

It is an additional object of the present invention to provide novel polyketones with aromatic, aliphatic or mixed aromatic/aliphatic backbones.

Other objects and advantages will become evident from the following detailed description of the invention.

BRIEF DESCRIPTION OF DRAWINGS

The foregoing and other objects, features and many of the attendant advantages of the invention will be better understood upon a reading of the following detailed description when considered in connection with the accompanying drawings, wherein.

DETAILED DESCRIPTION OF THE INVENTION

The above and various other objects and features of the present invention are achieved by employing $\alpha$-aminonitriles as monomers for the synthesis of high molecular weight aromatic, aliphatic or mixed aromatic/aliphatic polyketones. Polymerization of $\alpha$-aminonitriles has the particular advantage of producing a soluble precursor polymer retaining the aminonitrile functionality. Acid hydrolysis then yields the desired crystalline polyketone.

As noted in the literature[7,14], the extents of crystallinity and melting points of poly(arylene-ether-ketones) are a function of the proportions of ether and ketone functions in the backbone. And inclusions of more flexible backbone functionalities, such as alkylene or sulfone lead to a loss of crystallinity.[2] By use of aminonitrile chemistry, it is possible to include these functionalities in any desired proportions.

Among other advantages, the methodology of the present invention allows synthesis of macromolecules whose backbones consist exclusively of arylene and carbonyl moieties. Additionally, new types of polyketones, for example those containing $\alpha$-diketo moieties, are also produced by employing the methodology described herein. Furthermore, by applying this methodology to aliphatic systems, new classes of polymers such as homologs of olefin/carbon monoxide copolymers are also obtained. These new macromolecules are valuable for their crystallinity and associated mechanical performance and photodegradability.

A unique feature of the methodology of the present invention is that the polymerization produces the carbonyl moieties in a protected or masked state, causing the polymers to be amorphous and soluble, allowing high molecular weights to be achieved without exotic solvents and high temperature treatment. Then, by merely deprotecting the carbonyl moieties by conventional methods, e.g. by mild acid treatment, crystalline polymeric or copolymeric macromolecular materials having ketone functionality are obtained in the final processing step.

It is understood that unless mentioned otherwise all scientific and technical terms have the same meaning as understood by one of ordinary skill in the art. Except as described herein all methods used or contemplated herein are standard or conventional methodologies well known to a skilled artisan in the art to which this invention belongs. All references mentioned hereunder are hereby incorporated herein by reference.

As used herein, the term "soluble polymers" is defined as the polymers soluble in those commonly and ordinarily used, low boiling point, organic solvents, e.g. chloroform, toluene, benzene and the like, in which the important polyketones of the prior art, such as polyether-ether-ketone are insoluble. Depending on the structure, the polymers of the present invention may or may not be water soluble.

It is noted that the underlined Arabic numerals refer to the corresponding structural formula and the superscipt Arabic numerals refer to particular references listed at the end of the specification.

MATERIALS AND METHODS

Unless mentioned otherwise, the general reaction conditions are as follows.

(a) Polymerization:
Bases: NaOH, n-BuLi, NaH, LDA (lithium diisopropylamide), and the like.
Solvents: dimethylformamide (DMF); dimethylacetamide(DMAC); N-methylpyrollidinone (NMP); dimethyl sulfoxide (DMSO); tetrahydrofuran (THF); ether; water/toluene two phase system (for NaOH); and the like.
Temperature: −78 to 250 C.

(b) Deprotection:
Acids: Organic acids, such as acetic, oxalic, p-toluenesulfonic, trifluoroacetic; trifluoro-methanesulfonic; or mineral acids.
Solvents: organic acid, water, water/THF, water/dioxane, or one of the above-mentioned solvents by quenching into the acidic medium.
Temperature: 25–150 C.

Preparation

α-Aminonitriles (1) are readily prepared in high yields from aldehydes and secondary amines, for example by Strecker reaction[15,16].

$$\begin{array}{c} \text{CN} \\ | \\ \text{R}-\text{C}-\text{H} \\ | \\ \text{NR}' \end{array} \qquad 1$$

Depending on the nature of R, a variety of bases may be employed to abstract the acidic proton; for aryl derivatives NaOH, NaH, etc. may be used, while stronger bases (BuLi, LDA, etc.) are employed when R=alkyl.[16] Alkylation, Michael reactions and other nucleophilic displacement reactions may also be carried out with these anions. These are standard reaction mechanisms well known to skilled artisan.[16,17]

The α-aminonitrile 2 (Ar=phenyl unless noted) derived from benzaldehyde and morpholine is used herein to illustrate these transformations. Typically the reactions discussed are carried out under very mild thermal conditions at 0°–30° C. (or below where noted) in DMF using NaH as base to form the carbanion 3. Alkylation of 3 with ethyl bromoacetate (−60 to −70 C.) yields 4c.[17] Methyl iodide and 3 produce 5a via 4a in 96% overall yield,[18] while 5b results in 94% overall yield from isopropyl bromide.[18] Reaction of 3, Ar=p-anisyl with acrylonitrile produces 6 a quantitatively.[17] Likewise methyl methacrylate and methyl crotonate produce 6b and 6c in 96 and 98% yields, respectively.[16] Acidic hydrolysis of 6a and 6b led to ketones 7a and 7b in 94 and 95% yields, respectively.[17]

Reaction of acyl anion equivalent 3 with activated aromatic halides is exemplified by formation of 8a by reaction with p-fluoronitrobenzene; hydrolysis (acetic acid) gave 4-nitrobenzophenone (9a) in 89% overall yield.[17] Likewise p-cyanofluorobenzene produced 4-cyanobenzophenone (9b) in 88% overall yield via 8b and 2-nitro-4-trifluoromethylchlorobenzene afforded a 92% overall yield of 2-nitro-4trifluoromethylbenzophenone (9c) via 8c.[17]

Carbanions 3 react with acid chlorides (−60° to −70° C.) to produce intermediates 10, which upon hydrolysis form α-diketones 11. In the case of ethyl chloroformate the yield of 10, R=OC₂H₅ is 94%.[17]

Figure 1:
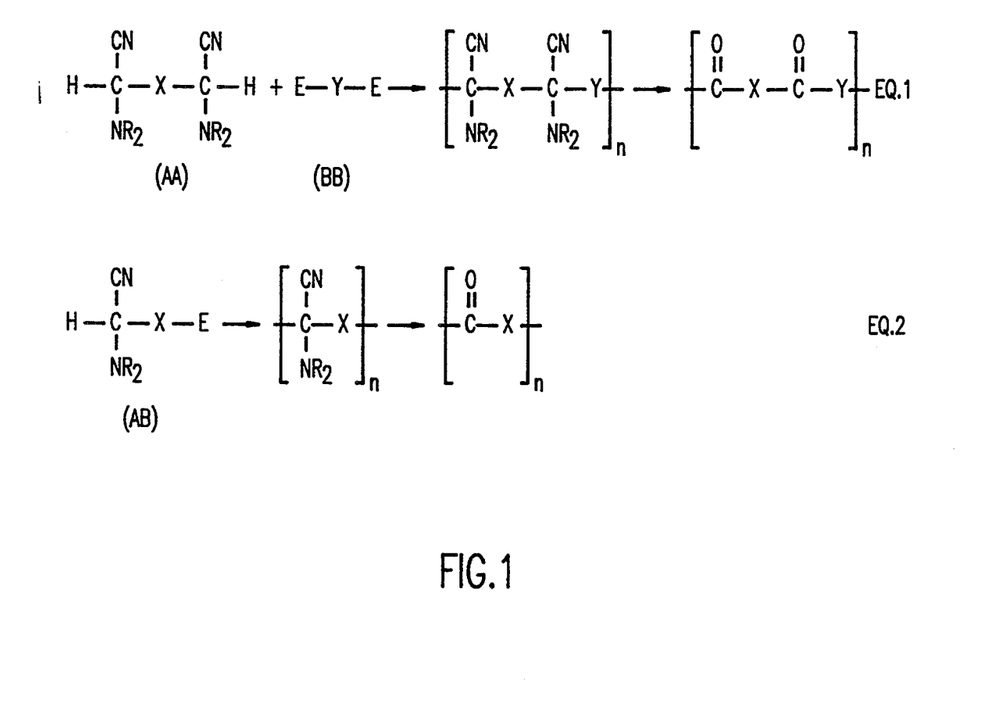
FIG. 1 shows the generic classes of monomers and polymers that may be formulated in accordance with the present invention. The letter E represents any electrophile and X and Y are aliphatic, aromatic or mixed aliphatic/aromatic.
Figure 2:
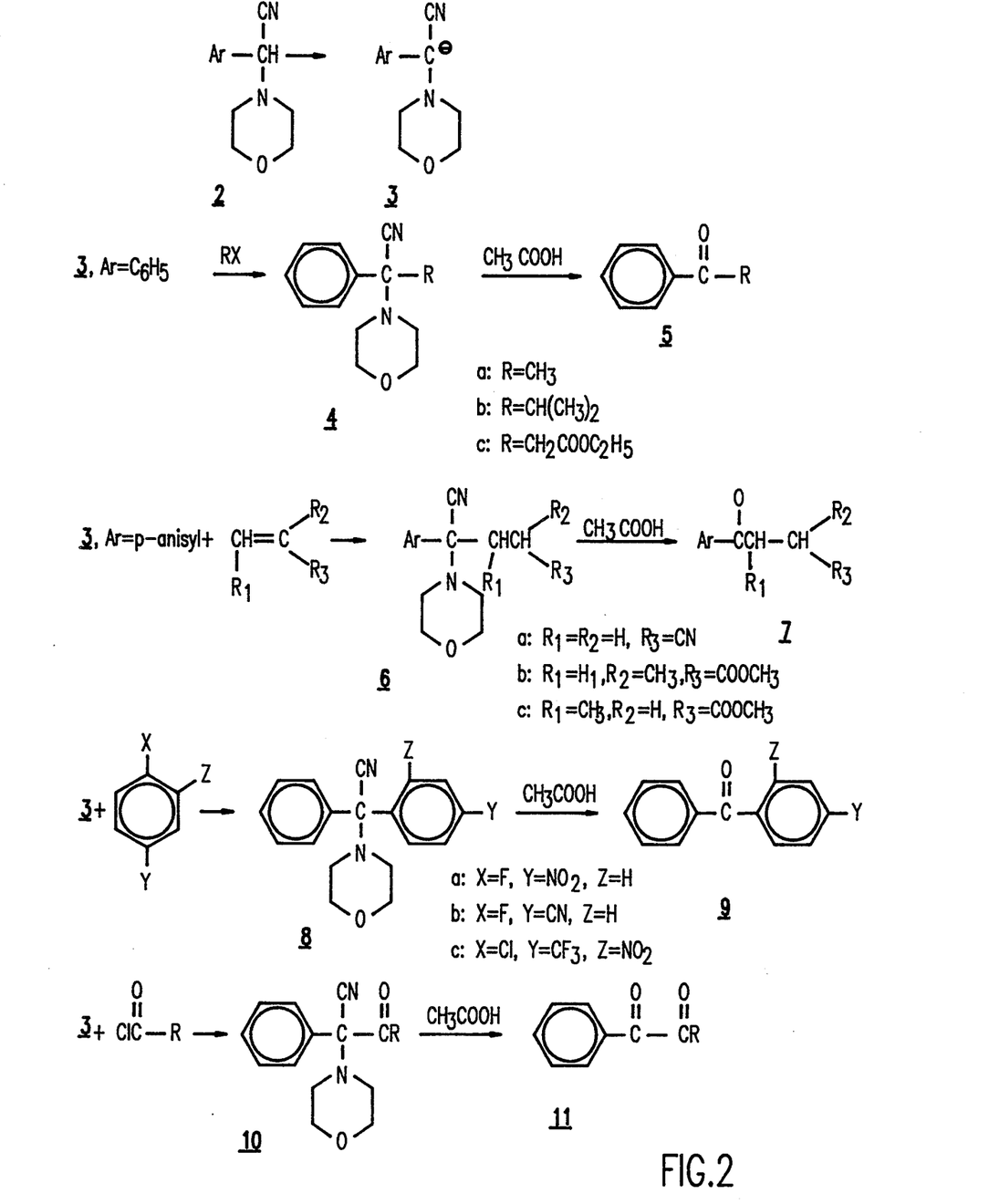
FIGS. 2-6 show the formulae of various reactants and products described in the present application.
Figure 3:
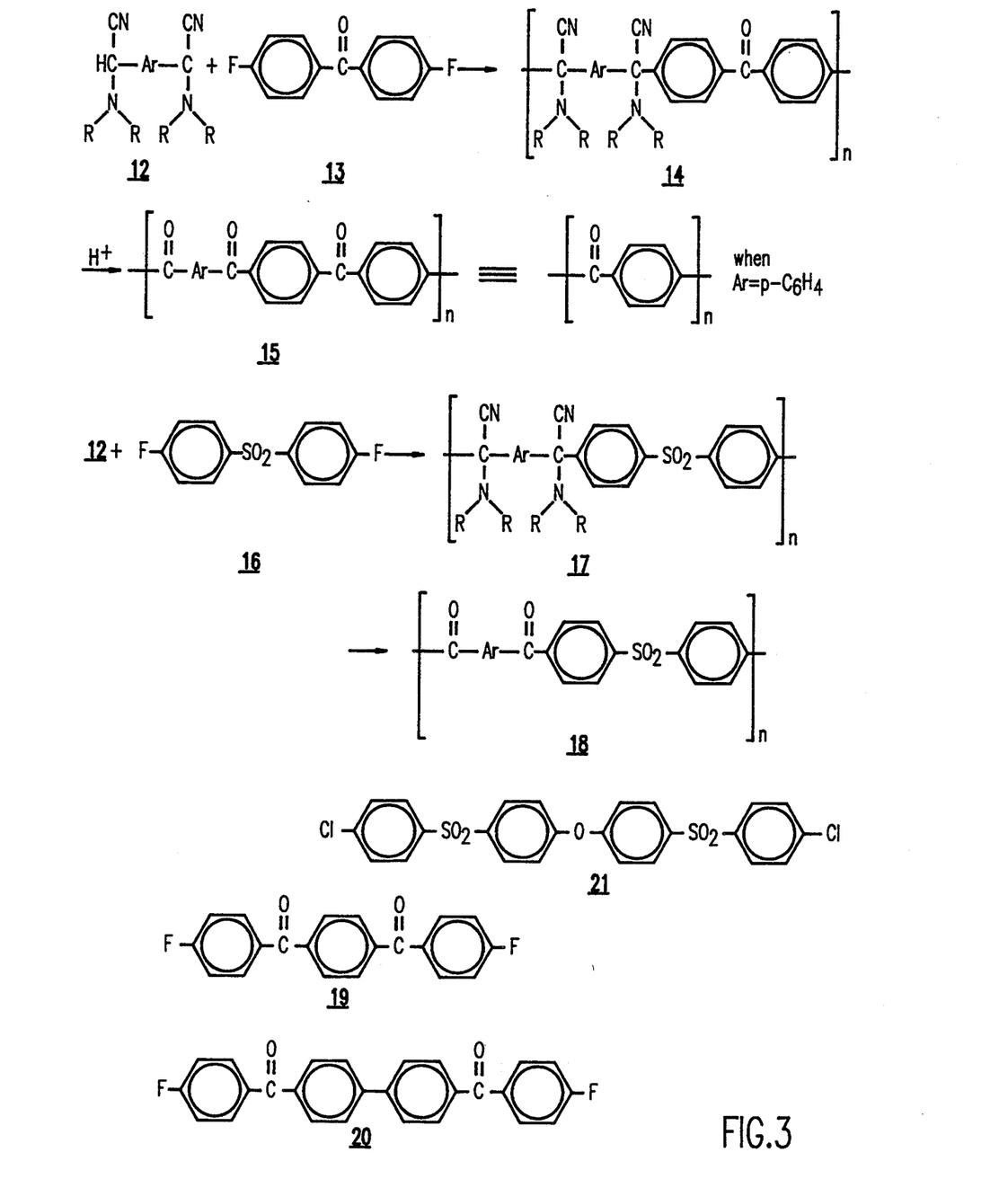
Figure 4:
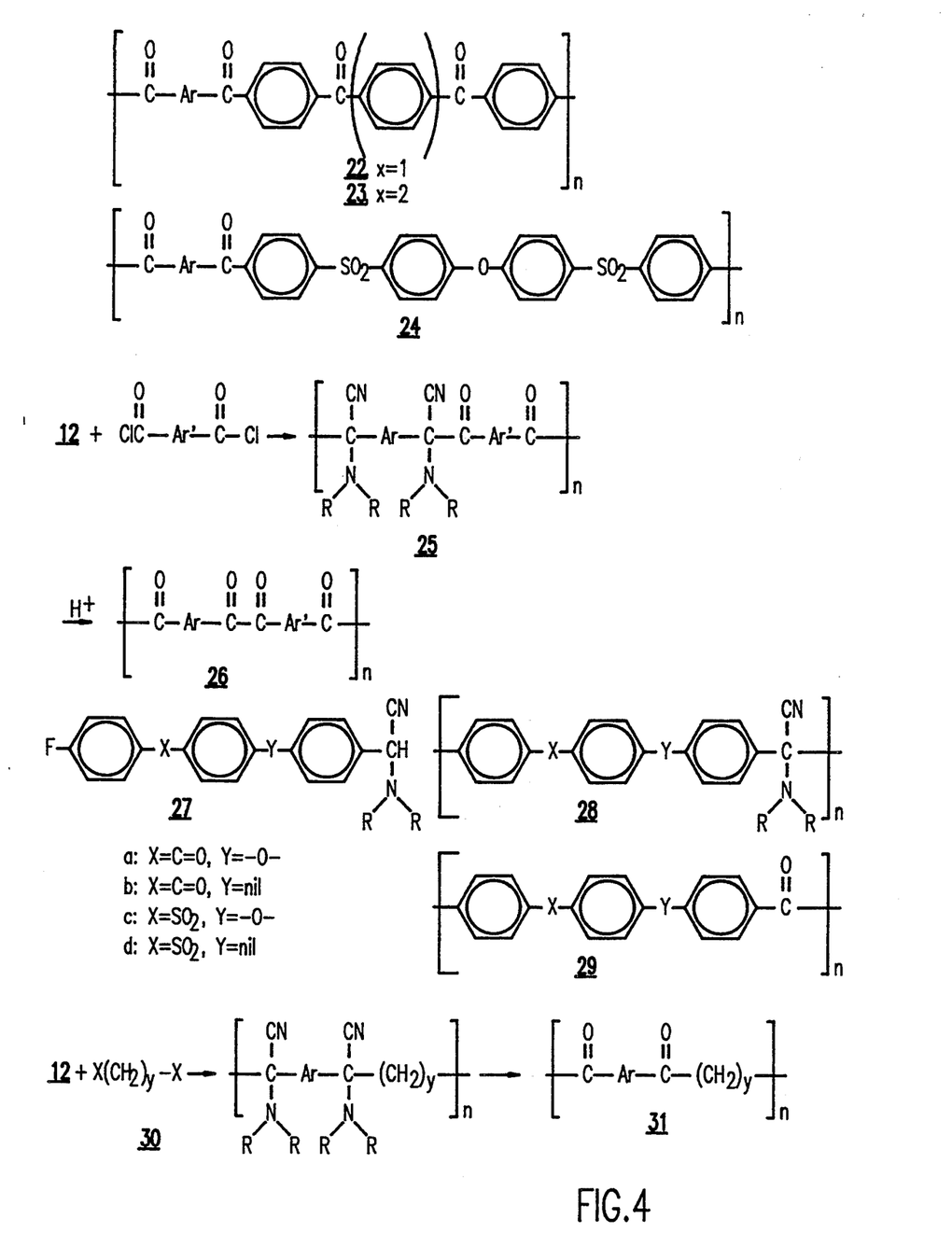
Figure 5:
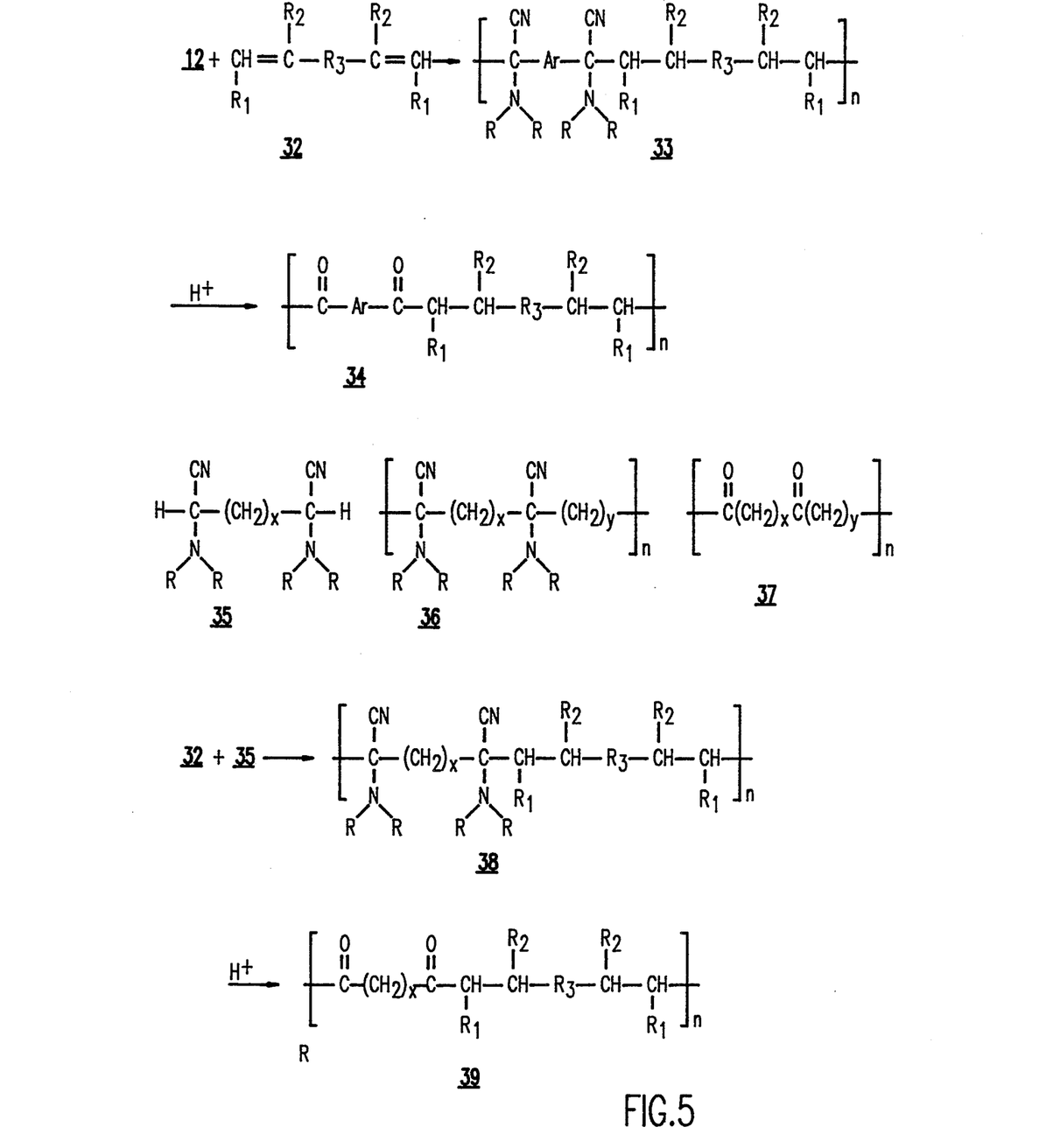
Figure 6:
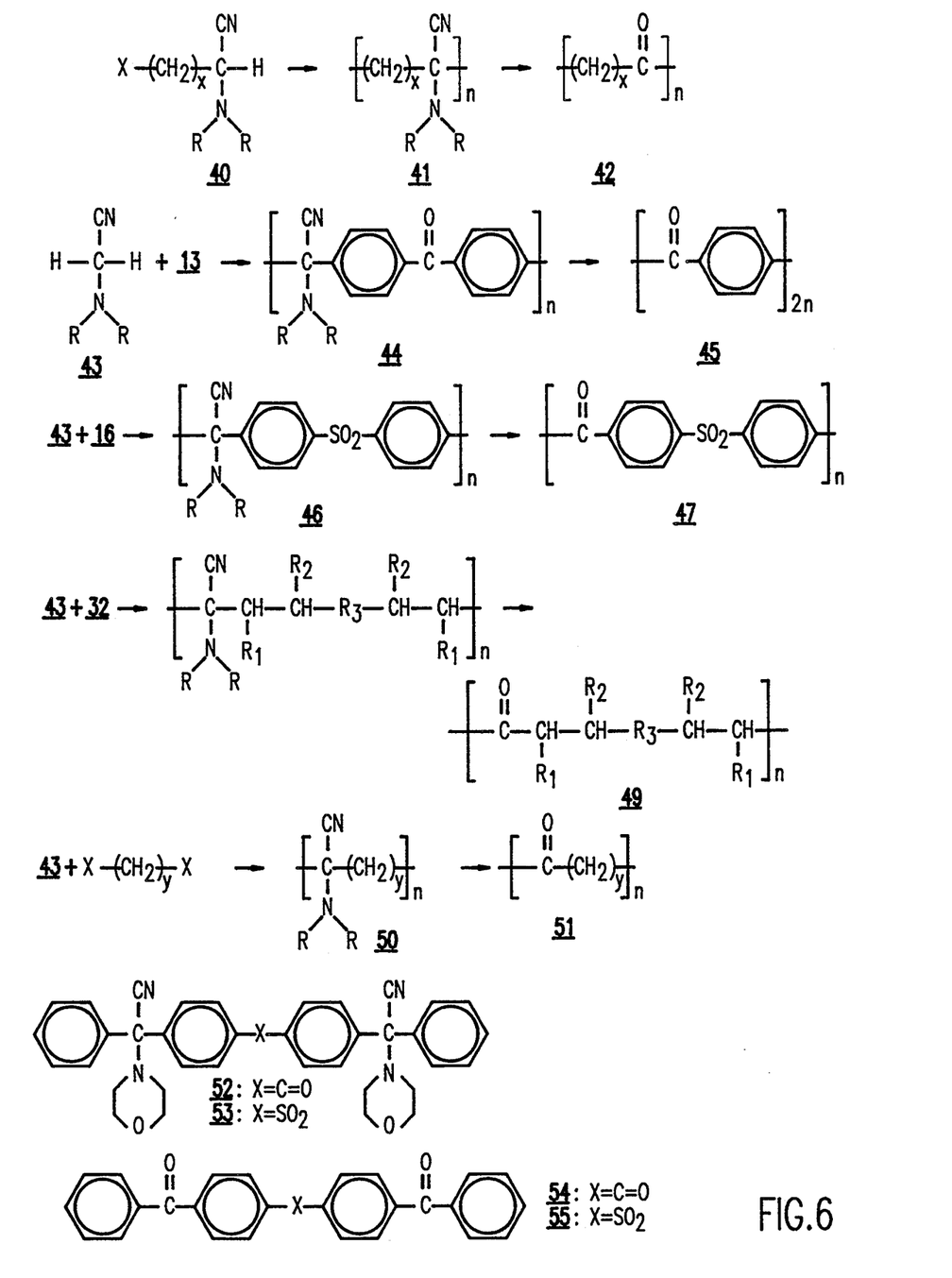

It should be noted that the use of acyl anion equivalents for polymerization in accordance with the requirements for step growth polymerizations must meet several criteria to produce high molecular weight products. Reactions must proceed to high conversion without side reactions. The high yields obtained for reactions of aminonitriles under unoptimized conditions are noteworthy in this regard. Premature precipitation must be avoided; since aminonitrile moieties are retained in the polymer, solubility is not a problem. The monomers must be difunctional, either of the AB or AA/BB type. The aminonitriles anions are reacted with electrophiles of the types such as alkyl halides, acid chlorides, activated aromatic halides and Michael acceptors. If E represents any of these electrophiles, a number of generic classes of new monomers and polymers may be formulated in accordance with equations 1 and 2 (EQ.1 and EQ.2) shown in FIG. 1.

A. AROMATIC POLYKETONES

Aromatic polyketones are products of either AA/BB (Eq.1) or AB (Eq.2) systems where X and Y are aromatic. For the first approach (AA/BB), reactions of bis(aminonitriles) derived from aromatic dialdehydes with either activated aromatics or acid chlorides are required.

New bis(aminonitrile)s 12 with difluorobenzophenone (13) produce the polyaroyls 15 via poly(aminonitrile ketone)s 14. These unique polymers (15) have the highest possible carbonyl content for such polymers and exhibit very high crystallinity and melting points. Hydrolysis by wet spinning of 14 through an acidic medium may be used to produce high performance fibers of 15.

Reaction of 12 and difluorodiphenylsulfone (16) produces the novel poly(sulfone ketone ketone) 18 via intermediate poly(aminonitrile sulfone) 17.

Extensions to the known activated aryl halides 19, 20 and 21 produce poly(ketone ketone ketone ketone)s 22 and 23 repectively, and poly(ether sulfone ketone ketone sulfone) ["PESKKS"] 24. Of course, copolymerizations are also possible.

Reactions of bisaminonitriles 12 with aromatic diacid chlorides produce the poly(α-diketones) or poly(benzil)s 26, via soluble intermediates 25. A variety of aromatic diacid chlorides are available, including terephthaloyl, isophthalolyl, oxydibenzoyl, and the like.

Figure 7:
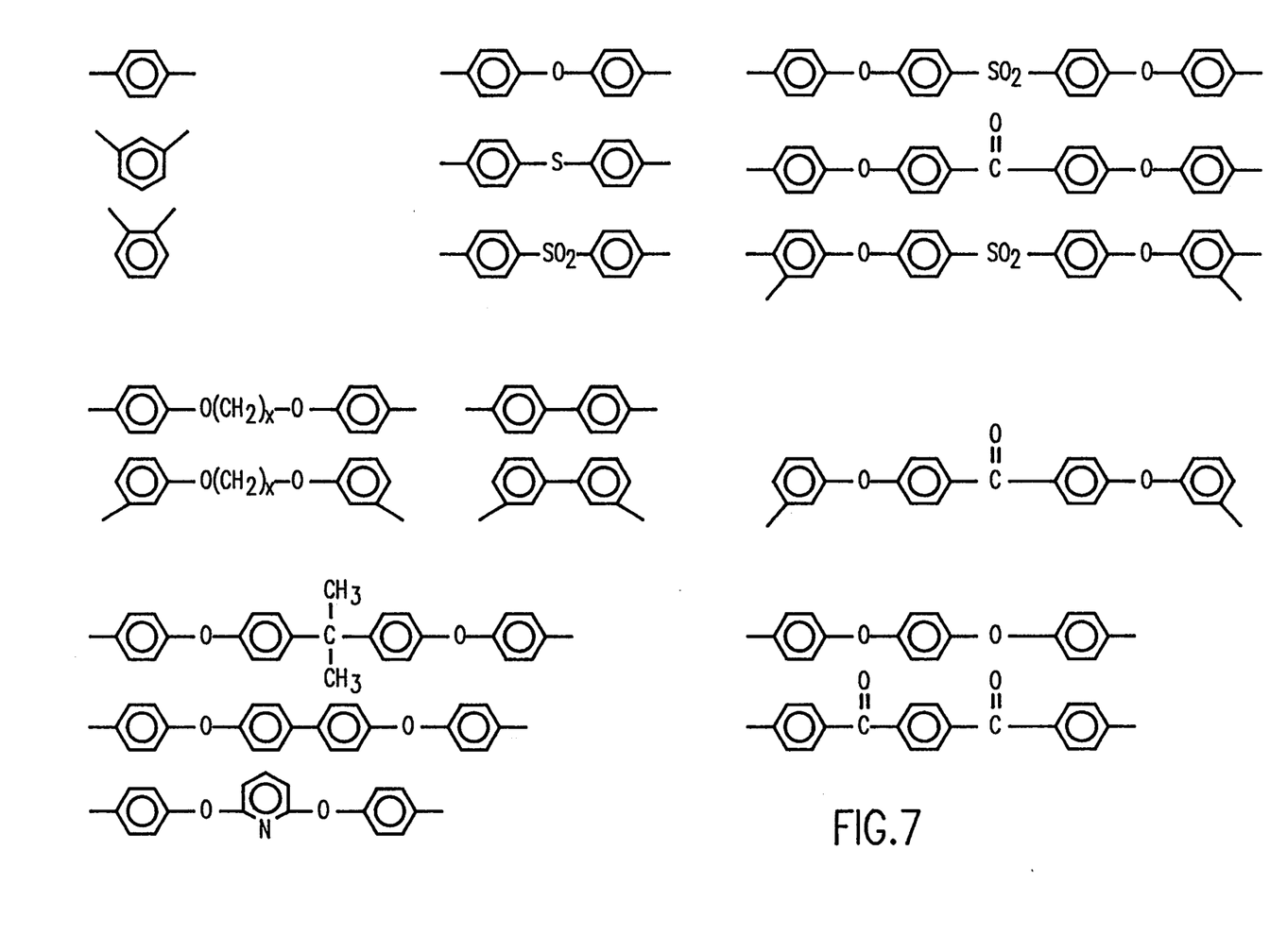
FIG. 7 shows representative structures of possible arylene groups in the monomers (e.g. in 12) and derivative polymers (e.g. 14, 15, 17, 18, 22, 26, 30, 31, 33, and 34), in accordance with the present invention.

The arylene group (∼Ar) in monomer 12 and derivative polymers (e.g., 14, 15, 17, 18, 22–26) may vary widely. Representative structures of such arylene groups are shown in FIG. 7.

Figure 8:
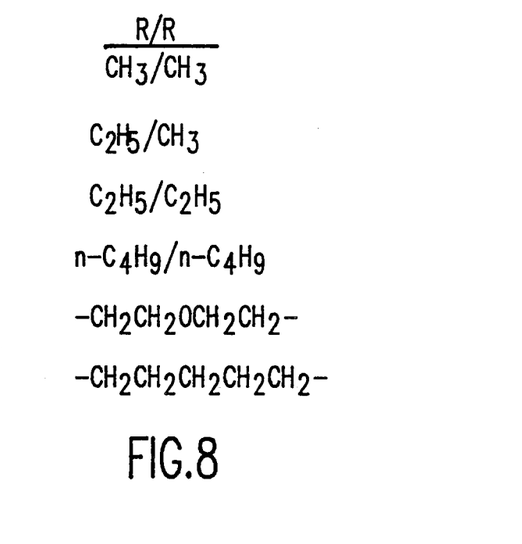
FIG. 8 shows representative examples of various R groups in 12, 27, and 35, and derivative polymers (e.g., 14, 17, 25, 28, 30, 33, 36, and 38).

The R group of 12 may also be varied so as to influence solubility and reactivity. The R groups listed in FIG. 8 are exemplary.

AB monomer systems 27 can also be prepared from suitable substituted benzaldehydes, which in turn are available by acylation or sulfonylation of 4-biphenylcarboxaldehyde or p-phenoxybenzaldehyde. These aminonitriles are precursors to polyketones 29 via intermediate poly(aminonitriles) 28. 29a is a poly(ether ketone ketone), 29b a poly(ketone ketone), 29c a poly(ether ketone sulfone) and 29d a poly(ketone sulfone). Of course, other similar AB monomers are considered within the scope of this invention.

B. ALIPHATIC POLYKETONES

Polyketones with aliphatic backbone components may also be prepared via aminonitrile chemistry from AA/BB or AB monomer systems as summarized in Eqs. 1 and 2, where X and/or Y are aliphatic.

First, reactions of bis(aminonitriles) derived from aromatic dialdehydes with aliphatic dihalides are considered. For example 12 with α,w-dihaloalkanes will produce polyketones 31 via 30. In fact aliphatic spacers have only recently been incorporated into poly(ether ketone)s for the first time. This hitherto unknown series of polymers[19] have a combination of the properties of aromatic polyketones and ethylene/CO copolymers. Crystallinity is expected with melting points intermediate between the former (~400° C.)[2,7] and the latter (110°-240° C.).[20] When y>2 enhanced photodegradability[13] is expected on the basis of increased UV absorbance brought about by the presence of the aromatic chromophore.

Figure 9:
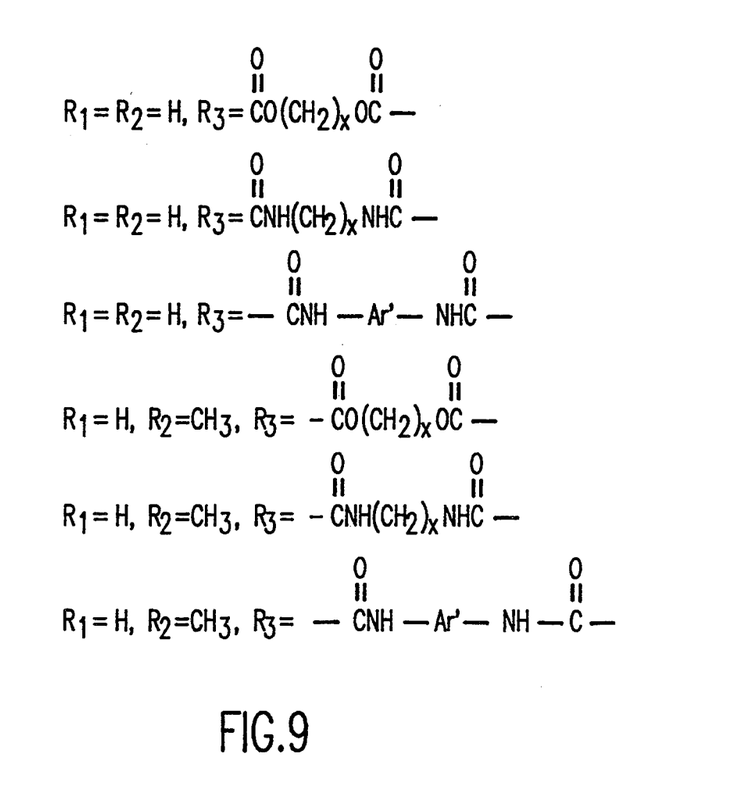
FIG. 9 shows representative examples of suitable divinyl compounds 32.

Michael reactions of 12 with suitable divinyl compounds 32 produce intermediate polymers 33 which are converted to poly(ketones) 34 by hydrolysis. Suitable examples of divinyl compounds 32 are shown in FIG. 9. Thus, the polymers 34 can be designed to be poly(keto ester)s, poly(keto amide)s, and the like.

Backbones consisting solely of alkylene and ketone moieties are synthesized from bis(aminonitriles) derived from aliphatic dialdehydes. Formation of the corresponding bis(aminonitriles) is straightforward. Although other aliphatic dialdehydes are included in the present disclosure, the most available dialdehyde is glutaraldehyde, leading to 35, X=3. Formation of the dianion of 35, X=3 followed by condensation with α,w-dihaloalkanes produces a family of poly(aminonitriles) 36 readily soluble and processable and easily converted under acid catalysis to aliphatic polyketones 37.

By variation of x and y in 37 a novel family of analogs of the ethylene/CO copolymers can be synthesized. In the case of 37 where x and y≦2, no γ-hydrogens are available for Norrish type II photodegradation and the polyketone will be stable and correspond to the next higher homolog of the alternating ethylene/CO copolymers, having three methylene groups between carbonyl pairs. For x or y>2 photodegradation is possible.[13]

Use of bis(Michael acceptors) 32 in reacting with 35 via intermediates 38 produces the aliphatic polyketones 39, again with incorporation of ester, amide, etc., linkages. This allows combinations of the properties of polyketones with those of polyesters, polyamides, etc.

The molecular weights achievable in these step growth polymerizations are subject to the usual constraints: stoichiometric equivalence, monomer purity and absence of side reactions. However, unlike the ethylene/CO copolymers made by free radical methods, these condensation polymers are free of branching and, therefore, crystallizable. Of course, these reactions may also be extended to substituted dihaloalkanes.

AB monomers 40 may be derived, for example, from haloaldehydes. Polymerization of these in the presence of a base leads to polyketones 42 via soluble intermediate polyaminonitriles 41. Here again x, the number of methylene units, is variable, enabling control of physical properties ($T_g$, $T_m$, etc.) and photodegradability.

These aliphatic polyketones (e.g., 31, 37, and 42) constitute a unique set of polyketones in terms of the range of composition and structural regularity. Especially noteworthy are the cases in which x is an odd number; such polyketones cannot be made by the usual free radical or Pd catalyzed insertion polymerization methodologies.

In the case of aliphatic systems, linkages other than linear or branched alkylene, such as oxyalkylene, aminoalkylene or thioalkylene, are considered within the scope of X/Y variations of Eq.1 and Eq.2 noted supra.

C. AROMATIC AND ALIPHATIC POLYKETONES FROM FORMALDEHYDE AMINONITRILES

Use of the AA monomeric aminonitriles 43 derived from formaldehyde enables synthesis of both aromatic and aliphatic and mixed aromatic/aliphatic polyketones. The aminonitrile functions as a carbonyl equivalent.[21] For example, reaction of 43 via its anion with 13 produces soluble 44 which can be converted to polyaroyl 45. Similarly, from 43 and 16, 47 results by way of soluble precursor 46. Reactions of 43 with bis(Michael acceptors) 32 lead to soluble precursor 48, which upon hydrolysis produces 49. Aliphatic polyketones 51 result via soluble precursor polymers 50 from reaction of dihaloalkanes with the anion of 43.

All of the advantages mentioned above, notably those of the control of the carbonyl content, $T_g$, $T_m$, molecular structure and photodegradability, accrue to the use of 43 in synthesis of polyketones.

EXAMPLE 1

α-(N-morpholino)benzyl cyanide (2,Ar=C$_6$H$_5$)

NaHSO$_3$, 10.5 g (100 mmol), was dissolved in 150 mL of water and 11 mL (100 mmol) of benzaldehyde were added and the mixture was stirred for 2 h until homogeneous. 8.7 mL (100 mmol) of morpholine were added in one aliquot and the stirring was continued for two more h. Finally, 5 g (100 mmol) of NaCN were added and the solution was stirred for 6 h at the end of which a shiny, white solid material precipitated out. The yield was 19.8 g (98%), mp=66.8°-67.8° C. It was recrystallized from 150 mL (1:1) hexane : EtOAc to yield shiny, white platelets, mp=67°-68° C. (lit.[16] 68°-70° C.). NMR (AP-2-88-17, CDCl$_3$) δ: 7.55-7.35 (m, 5H), 4.82 (s, 1H), 3.78-3.65 (m, 4H), 2.59-2.56 (t, 4H, J=4.7 hz). FTIR (AP-2-88-19): 2228 (CN), 1454 (methylene scissor), 1117 (C—O—C), 703, 739 (monosubstituted benzene).

EXAMPLE 2

4,4'-Bis(α-cyano-α-N-morpholino)benzyl benzophenone (52)

1.85 g (9.16 mmol) of α-(N-morpholino)benzyl cyanide (2, Ar=C$_6$H$_5$) was dissolved in 12 mL of dry DMF along with 1.00 g (4.58 mmol) of 4,4'-difluorobenzophenone (13) in a dry round bottom flask under N$_2$. After 15 m of stirring to homogenize the solution, 405 mg (9.23 mmol) of 60% NaH were added in one aliquot and immediately vigorous bubbling of H$_2$, a slight exotherm and a change in color to greenish were observed. Within about 15 m, the color had changed to pale honey and stayed that way for 12 h of stirring that was allowed. Upon quenching the reaction mixture into ten fold excess ice-water, a white precipitate was collected and dried, yield=2.67 g (100%), mp 80°-122° C. (diastereomeric). NMR (AP-2-95-14, CDCl3) δ: 8.00-7.00 (m, 9H), 3.90-3.70 (m, 4H), 2.70-2.40 (m, 4H).

EXAMPLE 3

4,4'-Bis(α-cyano-α-N-morpholino)benzyl Diphenyl Sulfone (53)

1.63 g (8.07 mmol) of α-(N-morpholino)benzyl cyanide (2, Ar=$C_6H_5$) was dissolved in 12.5 mL of dry DMF along with 1.04 g (4.04 mmol) of 4,4'-difluorophenyl sulfone (16) in a dry round bottom flask under $N_2$. After 15 m of stirring to homogenize the solution, 366 mg (17.7 mmol) of 60% NaH were added in one aliquot and immediately a vigorous bubbling of $H_2$, a slight exotherm and a change in color to greenish were observed. Within about 15 min, the color had changed to pale honey and stayed that way for 12 hour of stirring that was allowed. Upon quenching the reaction mixture into ten fold excess ice-water, a white precipitate was collected and dried, yield=2.51 g (100%), mp 125-165 C. (diastereomeric). The crude sample was crystallized thrice from DMF-EtOH and from benzene-hexane 3 times to yield white, shiny flakes mp 145-220 C. Elemental analysis found: C:70.96, H: 5.65, S: 4.89. This analysis fits very well with $C_{36}H_{34}N_4O_4S(0.5\ C_6H_6)$ i.e, with 1 mole of benzene as solvent of crystallization for every two moles of the compound (Calcd. C:71.21, H: 5.67, S:4.87). FTIR (AP-2-96-16/cm) : 1450 (methylene scissor), 1324, 1161 (sulfone), 1117 (C—O—C), 747 (monosubstituted benzene). NMR (AP-2-96-1, CDCl3) δ: 7.95-7.85 (m, 4H), 7.65-7.55 (m, 2H), 7.4-7.2 (m, 2H), 3.8-3.7 (m, 4H), 2.7-2.5 (m, 4H).

EXAMPLE 4

4,4'-Bis(benzoyl)diphenyl Sulfone (54)

1 g of 4,4'-bis(α-cyano-α-N-morpholino)benzyl diphenyl sulfone (52) was suspended in 25 mL of 70% AcOH and the mixture was refluxed. Within about 10 m, the solution had homogenized and in 5 more min, white solid started separating out. The mixture was cooled and the solid collected. Dry wt.=0.63 g (83), mp 192-195 C. It was recrystallized thrice from toluene-EtOH (9:1) to give shiny, colorless, fluffy crystals, mp 203.5-204 C. NMR (AP-2-93-20, CDCl3) δ: 8.11 (d, 2H, J=8.2 hz), 7.92 (d, 2H, J=8.2 hz), 7.79 (d, 2H, J=7.5 hz), 7.65 (dd, 1H, J+7.6, 7.3 hz), 7.51 (dd, 2H, J=8.2 hz), 7.79 (d, 2H, J=7.5 hz), 7.65 (dd, 1H, J=7.6, 7.3 hz), 7.51 (dd, 2H, J=7.7, 7.4 hz). FTIR (AP-2-93-23,/cm): 1668 (CO), 1654 (C=C arom.), 1331, 1165 (sulphone), 704 (monosubstituted benzene). Elemental analysis: found (calcd) for $C_{26}H_{18}O_4S$; C: 73.16 (73.22); H: 4.30(4.25); S: 7.77(7.52).

EXAMPLE-5

α,α'-Dicyano-α,α'-bis(N-morpholino-p-xylene (12, Ar=p-$C_6H_4$, R/R=$CH_2CH_2OCH_2CH_2$)

To a solution of 11.05 g (100 mmole) of $NaHSO_3$ in 300 mL of water were added 6.85 g (50 mmole) of terephthalaldehyde and the mixture was stirred for 2 h to give a homogeneous solution. 9.15 mL (100 mmol) of morpholine were added at this time and the solution was stirred for 2 more h to give a homogeneous solution of bis(aminal). A solution of 5.2 g (100 mmol) of NaCN in 100 mL of $H_2O$ was then added over a period of 2 h and the stirring was continued overnight. The pale cream solid was filtered and the dry crude solid weighed 16 g (100%), mp 224°-227° C. It was recrystallized from DMF - EtOH twice to yield off-white, shiny crystals, mp 230°-232° C. Elemental analysis: found (calcd. for $C_{18}H_{22}N_4O_2$): C: 66.50 (66.23), H: 6.75 (6.80), N: 17.23 (17.17). FTIR (AP-2-76-23): 2230 (CN), 1510 (C=C arom.), 1458 (methylene scissor), 1112 (C—O—C), 803 (p-disubstituted benzene). NMR (AP-2-76-9, CDCl3) δ: 7.61 (s, 2H), 4.85 (s, 1H), 3.85-3.69 (m, 4H), 2.7-2.52 (m, 4H).

EXAMPLE 6

Polymerization of Bisfluorophenyl Sulfone (16) and α,α'-Dicyano-α,α'-bis(N-morpholino)-p-xylene (12, Ar=p-$C_6H_4$, R/R=$CH_2CH_2OCH_2CH_2$) to form Poly(α-aminonitrile) 17, Ar=p-$C_6H_4$, R/R=$CH_2CH_2OCH_2CH_2$ a) At ca. 105° C.

3.026 g (9.271 mmol) of α,α'-dicyano-α,α'-bis(N-morpholino)-p-xylene (12, Ar=p-$C_6H_4$, R/R=$CH_2CH_2OCH_2CH_2$) were dissolved along with 2.3574 g (9.2719 mmol) of bisfluorophenyl sulfone (16) at 105° C. (solution temperature) in a flame dried flask in dry DMF under $N_2$. Upon the addition of 830 mg of 60% NaH (21 mmol), a vigorous bubbling and an immediate color change to deep maroon was seen. The solution was stirred for a total of 69 h and quenched in ice cold 5% aqueous NaCl to yield 4.97 g (99%) of a pale brown solid. Purification was done by dissolving it in 1:1 DMF:acetone and precipitation in water thrice. It was dried in a vacuum oven at 50° C. overnight. TGA (AP-3-12-16A): 10% weight loss (in air) at 252° C. followed by a 60% weight retention up to 500° C. and complete weight loss at 600° C. FTIR (AP-3-12-19, cm$^1$): 1676 (weak, CO), 1594 (arom. C=C), 1456 (methylene scissor), 1327, 1160 (sulfone) and 1117 (C—O—C). NMR (AP-3-12-21, CDCl3) δ: 8.12-7 48 (m), 3.97-3.63 (br. s), 2.72-2.38 (m). Absolute molecular weight determination (AP-3-61-2) by GPC (in NMP at 60° C.) displayed a $M_n$ of 345 g/mol and $M_w$ of 3300 g/mol respectively.

b) At ca. 25° C.

3.6223 g (11.098 mmol) of α,α'-dicyano-α,α'-bis(N-morpholino)-p-xylene (12, Ar=p-$C_6H_4$, R/R=$CH_2CH_2OCH_2CH_2$) were suspended along with 2.8216 g (11.098 mmol) of bis(fluorophenyl) sulfone (16) at ambient temperature in a flame dried flask in 25 mL dry DMF under $N_2$. The mixture was stirred for 20 minutes and stayed heterogeneous because of the insolubility of the bis(aminonitrile) at the reaction temperature. Upon the addition of 1.02 g of 60% NaH (23.0 mmol), a vigorous bubbling and an immediate color change to deep maroon was seen. The solution was stirred for a total of 120 h and quenched into 250 mL ice cold 5% aqueous NaCl to yield 6.05 g (100%) of a pale yellow solid. Purification was done by dissolving it in DMF and precipitation in water once. Then it was twice precipitated from a $CHCl_3$ solution into ten fold excess ice cold MeOH. It was dried in a vacuum oven at 50° C. overnight. TGA (AP-3-59-21): 10% weight loss (in air) at 268° C. followed by a 60% weight retention up to 500° C. and complete weight loss at 640° C. FTIR (AP-3-60-6, cm$^{-1}$): 1678 (weak, CO), 1591 (arom. C=C), 1452 (methylene scissor), 1331, 1158 (sulfone) and 1114 (C—O—C). NMR (AP-3-60-8, CDCl3) δ: 8.1-7.3 (m), 4.0-3.6 (br. s), 2.7-2.4 (m). An absolute molecular weight determination by GPC (AP-3-60-4)

yielded an $M_n$ of 5,000 g/mole and an $M_w$ of 15,000 g/mole.

EXAMPLE 7

Poly(sulfonyl-p-phenylenecarbonyl-p-phenylenecarbonyl-p-phenylene)(18, Ar=p-$C_6H_4$)

1.00 g of the above material 17 was refluxed in 25 mL 30% AcOH for 1.5 h, the product was filtered and dried thoroughly after washing exhaustively with water and MeOH, 0.65 g (100%). A reduction in total mass of 36% corresponds to quantitative hydrolysis of the aminonitrile groups. TGA (AP-3-59-20) showed a 10% weight loss at 491° C. (i.e., an increase of 233° C. after the removal of the aminonitrile moiety). It was insoluble in any solvent that was tried, including toluene, DMF, acetone and THF.

EXAMPLE 8

$\alpha,\alpha'$-Dicyano-$\alpha,\alpha'$-bis(N-morpholino)-m-xylene (12, Ar=m-$C_6H_4$,R/R=$CH_2CH_2OCH_2CH_2$)

To a solution of 11.2 g (100 mmol) of $NaHSO_3$ in 200 mL of $H_2O$ were added 7.0 g (50 mmol) of isophthalaldehyde (98%) and the mixture stirred to homogeniety for 2 h. 10 mL (106 mmol) of morpholine were then added in one aliquot and the solution was stirred for 2 h. 5.5 g (105 mmol) of NaCN were then added in one aliquot and the beaker was transferred to a steam bath where it was heated for 8 h with occasional stirring. The filtered pale yellow solid was dried to yield 15.9 g (100%) of product which was crystallized twice from 95% EtOH to obtain a pale yellow powder, mp 118.5°–135.5° C. After thorough drying, it was placed in a fritted disc funnel, washed with 200 mL of 95% EtOH by gravity filtration and dried in a vacuum oven at 60° C. overnight. NMR (AP-3-75-18, $CDCl_3$) showed peaks at $\delta$ 7.70 (d, 1H, J=11.9 hz), 7.59 (d, 2H, J=7.4 hz), 7.50-7.44 (dd, 1H, J=6.8 hz, 8.53 hz), 4.85, 4.84 (1H, diastereomeric acidic proton), 3.9-3.7 (m, 8H) and 2.8-2.5 (m, 8H). FTIR (KBr disc, $cm^{-1}$): 2228 (v. v. weak, CN), 1456 (phenyl), 1113 (C—O—C) and 760 (m-disubs. phenyl). Elemental analysis: found (calcd. for $C_{18}H_{22}N_4O_2$): C: 66.23 (66.24), H: 6.80 (6.80) and N: 17.14 (17.17).

EXAMPLE 9

Polymerization of Bis(fluorophenyl) Sulfone (16) and $\alpha,\alpha'$-Dicyano-$\alpha,\alpha'$-bis(N-morpholino)-m-xylene (12, Ar=m-$C_6H_4$, R/R=$CH_2CH_2OCH_2CH_2$) to form Poly($\alpha$-aminonitrile) 17, Ar=m-$C_6H_4$, R/R=$CH_2CH_2OCH_2CH_2$ 3.6608 g (11.216 mmol) of $\alpha,\alpha'$-dicyano-$\alpha,\alpha'$-bis(N-morpholino)-m-xylene (12, Ar=m-$C_6H_4$, R/R=$CH_2CH_2OCH_2CH_2$) were dissolved along with 2.8520 g (11.217 mmol) of bis(fluorophenyl) sulfone (16) at ambient temperature in a flame dried flask in dry DMF under $N_2$. The mixture was stirred for 20 minutes and was completely homogeneous at room temperature. Upon the addition of 1.04 g (24.5 mmol) of 60% NaH, a vigorous bubbling and an immediate color change to pale yellowish and then yellowish green was seen. After 24 h, the color of the reaction mixture was brown and the temperature was raised to 50° C. and the stirring continued. The color changed to a pale orange in 0.5 h and was pale honey after 24 h of stirring at 50° C. The temperature was then raised to 72° C. and stirring continued for 24 h, at the end of which an increase in the solution viscosity was evident. The solution was quenched in ice cold 5% aqueous NaCl to yield 6.1 g (100%) of a pale yellow solid. Purification was done by dissolving it in DMF and precipitation into water. Then it was twice precipitated from $CHCl_3$ solution into ice cold MeOH. It was dried in a vacuum oven at 50° C. overnight. TGA (AP-3-68-8): 10% weight loss (in air) at 298° C. FTIR (AP-3-67-23, $cm^{-1}$): 1678 (weak, CO), 1591 (arom. C=C), 1452 (methylene scissor), 1331, 1158 (sulfone) and 1114 (C—O—C). NMR (AP-3-67-21, $CDCl_3$) $\delta$: 8.2-7.2 (m, 12H), 4.0-3.5 (br. s, 8H), 2.7-2.2 (br. s, 8H). DSC (AP-3-68-20) showed a relatively large exotherm at 278° C., indicative of some reaction on the first heat. On the second heat, the maximum had shifted beyond the range of heating (i.e., at ca. 370° C.). Absolute molecular weight determination by GPC (AP-3-68-14) yielded a $M_n$ of 32,300 g/mole and a $M_w$ of 44,000 g/mole.

EXAMPLE 10

Poly(sulfonyl-p-phenylenecarbonyl-m-phenylenecarbonyl-p-phenylene) (18, Ar=m-$C_6H_4$)

1.0 g of the above material (17, Ar=m-$C_6H_4$, R/R=$CH_2CH_2OCH_2CH_2$) was refluxed in 25 mL 30% AcOH for 1.5 h, filtered and dried thoroughly after washing exhaustively with water and MeOH, 0.65 g (100%). A reduction in total mass of 36% corresponds to quantitative hydrolysis of the aminonitrile groups. TGA (AP-3-68-9) showed a 10% weight loss at 478° C. (i.e., an increase of 180° C. after the removal of the aminonitrile moiety). An absolute molecular weight determination by GPC (AP-3-68-17) yielded an $M_n$ of 16,400 g/mole and an $M_w$ of 30,600 g/mole. DSC (AP-3-68-23) showed a $T_g$ of 192° C. on the first heat, a crystallization exotherm with a maximum at 242° C. and a $T_m$ of 257° C. On the second heat, a $T_g$ of 195° C. was noted with no signs of $T_m$.

It is understood that the description and examples etc., provided herein are only exemplary and not limiting and that various modifications and changes in light thereof may be suggested to one of ordinary skill in the art and all such changes and modifications are deemed to be within the purview and scope of the present invention and accompanying claims.

REFERENCES

1. R. May in Encyclopedia of Polymer Science and Engineering, J. Wiley & Sons, N.Y., 2nd ed., 1987, Vol 12, pp 313–320.
2. P. A. Staniland in Comprehensive Polymer Science, G. Allen and J. C. Bevington, series eds. Pergamon Press, N.Y., Vol. 5, 1989, pp. 483–497.
3. Colquhoun, H. et al, J. Chem. Soc., Chem. Commun., 1990, 336.
4. Ueda M. et al, Macromol. 1990, 23:926.
5. Johnson et al, Polymer. J. Polym. Sci. Al, 1967, 5:2375.
6. Attwood, et al, Polymer, 1977, 18:354.
7. Atwood et al, Polymer, 1981, 22:1096.
8. Kircheldorf, et al, Polymer, 1984, 25:1151.
9. Kircheldorf, et al, Macromol. 1989, 22:517.
10. U.S. Pat. No. 3,442,857; Chem. Abstr. 1967, 67:44371.
11. U.S. Pat. No. 3,516,966; Chem. Abstr. 1970, 73:35968.
12. Eur. Patent 63,874; Chem. Abstr. 1983, 98:180081.

13. Starkweather in Encyclopedia of Polymer Science & Engineering, J. Wiley & Sons., N.Y., 2nd.ed., 1987, Vol. 10, pp 369–373.
14. Harris et al, J. Polym. Sci. Poly. Phys. Ed. 1987, 25:311.
15. March, Advanced Org. Chem., J. Wiley & Sons., N.Y., 3rd ed., 1985, pp 855–856.
16. Albright, J., Tetrahedron, 1983, 39:3207.
17. McEvoy, et al, J. Org. Chem. 1979, 44:4597.
18. Albrecht et al, Synthesis, 1979, 127.
19. Kircheldorf et al, Macromol., 1989, 22:517.
20. Starkweather, H., J. Polym. Sci., Polym. Phys. Ed., 1977, 15:247.
21. Stork, et al, Tetrahedron Ltrs., 1978, 5175.

We claim:

1. A method of preparing polymers having ketone functionality, comprising the steps of:
   forming a dianion from a first monomer having at least one aminonitrile constituent, wherein the amino moiety of the aminonitrile constituent is a secondary amine;
   condensing said dianion with a difunctional electrophile to produce a polyaminonitrile; and
   acid catalyzing aminonitrile constituents in said polyaminonitrile to produce a polymer having ketone functionality.

2. A polymeric material having ketone functionality having the formula:

where Ar is selected from the group consisting of:

3. The polymeric material of claim 2 wherein Ar is:

4. The method of claim 1 wherein said step of forming a dianion is achieved by reacting said monomer with a base which will remove a hydrogen from said aminonitrile constituent.

5. The polymeric material of claim 2 wherein Ar is selected from the group consisting of:

6. The polymeric material of claim 2 wherein Ar is:

* * * * *